United States Patent [19]

Thewalt et al.

[11] 4,448,999

[45] May 15, 1984

[54] PROCESS FOR THE PREPARATION OF 2-AMINOPROPANEDIOL-1,3(SERINOL)

[75] Inventors: Klaus Thewalt, Witten; Gunter Bison, Troisdorf-Sieglar, both of Fed. Rep. of Germany; Heinz Egger, Muttenz, Switzerland

[73] Assignee: Dynamit Nobel Aktiengesellschaft, Troisdorf, Fed. Rep. of Germany

[21] Appl. No.: 403,326

[22] Filed: Jul. 30, 1982

[30] Foreign Application Priority Data

Jul. 30, 1981 [DE] Fed. Rep. of Germany ....... 3130082

[51] Int. Cl.³ ............................................. C07C 85/11
[52] U.S. Cl. ................................................... 564/495
[58] Field of Search ......................................... 564/495

[56] References Cited

U.S. PATENT DOCUMENTS

| | | | |
|---|---|---|---|
| 2,587,572 | 2/1952 | Tryon | 564/495 |
| 3,564,062 | 2/1971 | Tindall | 564/495 X |
| 4,221,740 | 9/1980 | Pfeiffer | 564/495 |

*Primary Examiner*—Paul F. Shaver
*Attorney, Agent, or Firm*—Antonelli, Terry & Wands

[57] ABSTRACT

2-Aminopropanediol-1,3 (serinol) can be prepared by hydrogenation of the alkali salt of 2-nitro-1,3-propanediol with assuredly high yields by maintaining a narrow range of temperatures of extending from 50°–80° C. by use of a cooling device.

7 Claims, 1 Drawing Figure

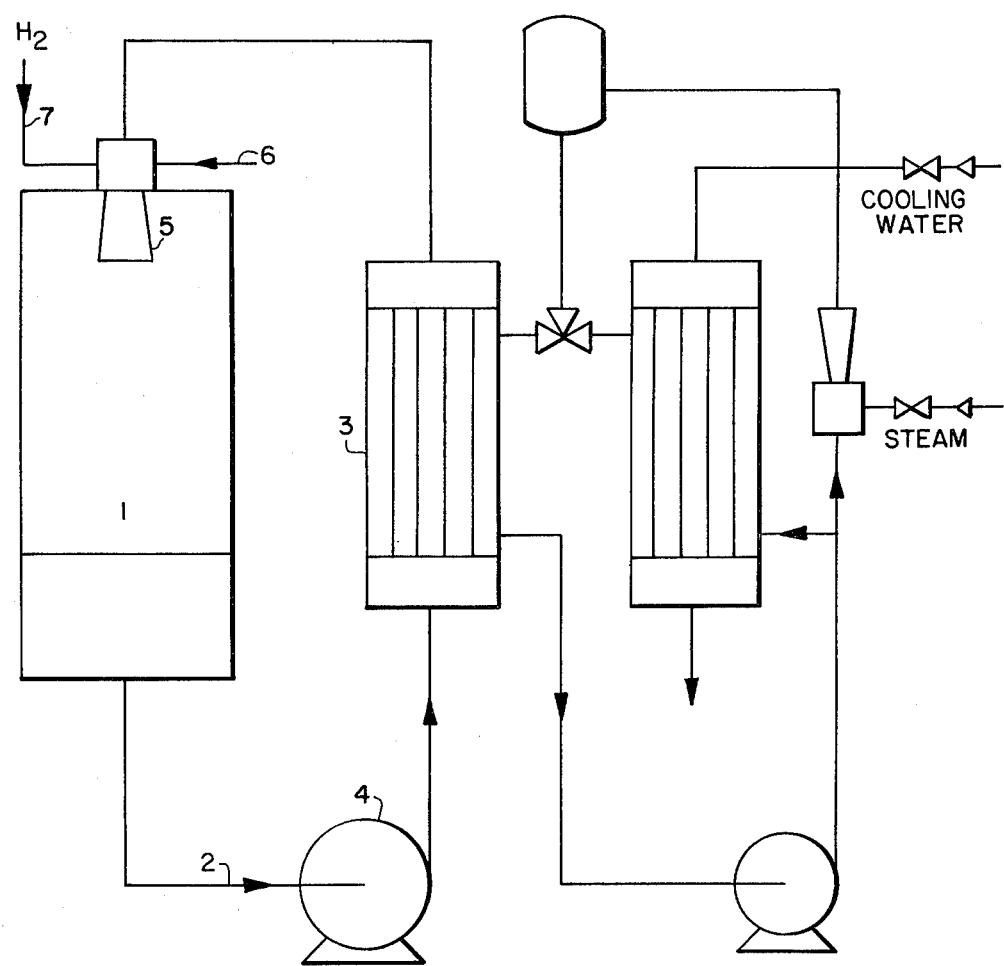

PROCESS FOR THE PREPARATION OF 2-AMINOPROPANEDIOL-1,3(SERINOL)

The invention relates to a process for the industrial production of 2-aminopropanediol-1,3 (serinol).

Serinol is an intermediate for the preparation of X-ray contrast media, especially iopamidol (N,N'-bis[2-hydroxy-1-(hydroxymethyl)ethyl]-2,4,6-triiodo-5-lactamidisophthalamide).

According to the prior art, serinol can be prepared, inter alia, from 2-oximino-1,3-propanediol, 2-nitro-1,3-propanediol, serine, serine methyl ester, or oximinomalonic acid diethyl ester.

These manufacturing processes exhibit the disadvantage of unsatisfactory yields and, in part, poorly accessible starting materials. Decomposable and dangerous by-products are formed which can be removed only with difficulties and expenses.

According to German Pat. No. 2,742,981, serinol can be prepared by hydrogenation of the sodium salt of 1,3-dihydroxy-2-nitropropane (2-nitro-1,3-propanediol), optionally in the presence of a buffered acid. Repeating the examples set forth therein at 10° C. as well as 27° C. resulted in markedly lower yields than those set forth in the patent. Repeating the process under identical conditions resulted in serinol with, in part, low and greatly fluctuating yields although the stoichiometric quantity of hydrogen was always absorbed. Occasionally, for example, 30% serinol or, on another occasion, 50% serinol yields were produced, but differing amounts of unstable by-products prevented processing of the reaction mixture.

Reactions of 2 kg of sodium nitro-1,3-propanediol in methanol in the presence of ammonium chloride with 0.11 kg of 5% Pd/C at 50 bar yielded, in one instance, no product in spite of long hydrogenation periods; the next instance compounds were obtained which decomposed during the working-up process, and another time resinous condensation products were the result. Insofar as minor amounts of serinol were produced, by-products could not be removed. A temperature elevation to 30°–50° C. did result in shorter hydrogenation times, but the formation of resinous and unstable by-products was even more increased. In an agitator-equipped autoclave, the characteristic outcome was that, when repeating the procedure under identical conditions, entirely different products occurred; consequently, reproducibility is not present. Above about 25° C., reactions in the stirred autoclave proved to be useless under any conditions.

Therefore, the task presented itself of producing serinol by means of a reproducible process with constant success on an industrial scale in relatively large quantities and assured, if possible, increased yields.

This invention is directed to a process for the preparation of 2-aminopropanediol-1,3 by the catalytic hydrogenation of an alkali salt of 2-nitro-1,3-propanediol in the presence of inert solvents and a buffered acid under pressures of 1–98 bar hydrogen, while maintaining the temperature in a narrow range of temperature extending from 50°–80° C. by use of a cooling device during the reaction; i.e., for a period of time of from 15 to 300 minutes.

Hydrogenation is accomplished with hydrogen gas, which gas can additionally contain inert gases; e.g., from 5 to 50 vol% of e.g. $N_2$ or Ar. Suitable catalysts for the reaction are the platinum metals Pt, Pd, or Rh; nickel; cobalt; and mixed catalysts of these metals as precipitated metallic powders or applied to supports. Suitable buffered acids are salts of weak bases with strong or medium-strong mineral acids, especially ammonium chloride, ammonium sulfate, or ammonium phosphate.

It is very much preferred to add the buffered acid in equivalent amounts (i.e., e.g. 100 to 120 Mol% of $NH_4Cl$ referred to the starting compound.

Thereby, it is believed that during the reaction sequence, the alkali is initially split off from the alkali salt of the nitropropanediol, so that serinol is surprisingly formed, in the final analysis, from the free nitropropanediol in an alkalinized, alcoholic solution, according to the equation:

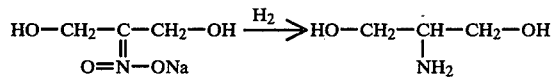

This free nitropropanediol is so readily decomposed, in all attempts at isolation, that its use as a starting compound is impossible.

The alkali salts of nitropropanediol are preferably utilized in the form of a suspension; i.e., in methanol.

The addition product of the nitropropanediol contains two moles of alkohol, especially methanol, is especially preferred; i.e., the so-called aci salt (i.e., a salt of a pseudo acid) for use as the starting compound.

The reaction is conducted in the presence of inert solvents, especially alcohols of 1–4 carbon atoms, preferably methanol; water can be present. Very preferably, the reaction is carried out while maintaining the narrow temperature range of 55°–60° C. during the entire reaction. This temperature, in the semibatch process, is to be set prior to beginning of the reaction. Best results are achieved with an almost isothermic procedure; this causes considerable difficulties at the high reaction heat and the desired, rapid conversion, which must be controlled by rapid removal of the heat.

It has been concluded from experiments that the high heat of reaction, especially with a sudden onset of hydrogenation, can only be controlled with a high-efficiency cooling device and, in some cases, with a metered feeding of the starting materials during the reaction and, on the other hand, that surprisingly only a narrow range of temperatures extending from 50°–80° C. lead to success. Although precisely at temperatures varying from 50°–80° C. in accordance with the German Pat. No. 2,742,981, the yield is entirely or quite predominantly only decomposition products or by-products, without the use of a cooling device to maintain the temperature within a narrow range and preferably in an isothermal state. Temperatures lying below this range are unsuitable; although the German patent indicated such temperatures to be solely suitable for the formation of serinol, though at only low yields and lack of reproducibility.

However, in accordance with the present invention, reactions of, per batch, 100–2,000 kg are possible, without incurring any danger, and resulting in quite superior yields of a product of high purity.

We found that, in the batch process, at 50°–80° C. and with a very efficient cooling device, the hydrogen absorption must take place within the first 15 minutes of the reaction, better still within 10 minutes, to an extent of at least 50%, preferably 60–70% or more, so that highest requirements must be met by the cooling device and the feeding means for the hydrogen.

The best feeding means for the hydrogen proved to be a mixing nozzle, arranged at the end of the ring conduit emanating from the reactor and returning into the reactor, with the cooling unit disposed therein, and effecting an intimate mixing of the reactants with the aid of high shearing forces.

A cooling device located outside of the reactor is preferred as the high-efficiency cooling means.

Very much preferred is a cooling device in a ring conduit emanating from the reactor and returning to the reactor. The cooling area of the cooling device, especially a large-sized heat exchanger, is to be dimensioned so that with a pumping efficiency of 5–70 reactor volumes per hour, the reaction temperature can be maintained with an accuracy of 3°–5° C., preferably 1°–2° C., even during a sudden and vigorous onset of the reaction.

Pressures of 20–80 bar are preferred.

A loop-type reactor is especially suitable as the reactor with a ring conduit and a cooling means disposed therein. Loop-type reactors of the model BUSS-SR (manufacturer BUSS AG, Basel (Switzerland) proved to be suitable.

The process of this invention will be further understood from the following detailed description and the accompanying drawings wherein the sole FIGURE, schematically, shows a loop-type reactor equipped with a cooling device.

The cooling device constructed as a heat exchanger 3 also permits heating up of the batch to the reaction temperature prior to onset of reaction.

The hydrogen is feed via conduit 7 into the mixing nozzle 5, simultaneously with an extremely finely divided reaction material recycled from the reactor into the gas space of the reactor (a liquid level is maintained in the reactor). It will be seen that the reaction products and unreacted reactants are passed via ring conduit 2 and pump 4 through the heat exchanger 3 which serves as a cooling device during the batch reaction. It will be appreciated that the reactor is initially charged with the alkali metal salt of 2-nitro-1,3-propanediol and admixed with appropriate amounts of the catalyst, the solvent, and the buffered acid.

The reaction can also be carried out, though not with equally high success, with a cooled stirrer-equipped autoclave, for example, a reciprocating-stirrer autoclave. In such cases, care must be taken, on the one hand, to provide a large cooling surface in the form of a jacket cooler, a cooler located inside the reactor; or, optionally, a cooling device disposed in a ring conduit, and simultaneously thorough intermixing must be effected during the reaction.

It must be noted as being pronouncedly surprising that, according to the process of this invention, the hydrogenation takes place at temperatures of predominantly 55°–60° C., because it could not be expected, according to the prior art, that this elevated temperature favors the formation of serinol without creating, simultaneously, the by-products typical for temperatures above 30° C. to the extent as is the case in the arrangement according to the examples in German Pat. No. 2,742,981. It must surprise anyone that, in spite of the increase in temperature in the present process as compared to the examples in German Pat. No. 2,742,981, very reactive intermediate stages occurring during hydrogenation in an alkaline medium, such as, for example, nitroso, hydroxylamine, azoxy, or azo compounds, fail to occur at all or occur only in insignificant amounts. The technical advantages of our process are obvious and reside, in particular, in the capability of reacting large quantities, obtaining very good yields and purities, an assured reproducibility, and thus the possibility of conducting the process on a large industrial scale without danger. Troublesome and time-consuming purifying steps in processing the hydrogenation batch are unnecessary. In particular, it is unnecessary to conduct the extraction of the hydrogenation mixture with isopropanol to remove resinous by-products, recommended in German Pat. No. 2,742,981, which, in the presence of large proportions of accompanying substances, is difficult and uneconomical.

Examples 1–8 concern the execution of the process as a batch process, adding all compounds for the charge (batch) at the beginning and heating while adding hydrogen. Example 9 relates to a semibatch process with metered feeding of the compounds through conduit 6 during the reaction under isothermic conditions.

Hydrogen is always provided in excess. Especially, within said range of the temperature of 50° to 80° C., it is mostly preferred maintaining the temperature of every run or batch at isothermic conditions what will mean in a range of about 3° or 4° C., or in practical cases within ±2° C. of, if possible, within ±1° C. That means for example a temperature of 57±2° C., or 60±2° C. or 55±2° C. or a range of 68±2° C. Therefore isothermic conditions are mostly preferred, wherein a basis temperature between 55 to 60 is predetermined; the so fixed temperature will vary during every run or batch within ±3 or better ±2 or best ±1 Celsius degrees.

EXAMPLE 1

A 1,400-liter loop-type reactor of the type shown in the drawing is charged with 680 kg of methanol, 175 kg (844 moles) of sodium salt of 2-nitro-1,3-propanediol (x2CH$_3$OH), 45.2 kg (844 moles) of ammonium chloride, and 8.0 kg of catalyst (5% Pd/C, 50% water-moist). Hydrogenation is started at 60 bar hydrogen pressure and room temperature by introducing hydrogen to the reactor. By heating within the heat exchanger 3 wherein steam is initially introduced, the hydrogenation batch is heated within 10 minutes to 55±2° C. and maintained at this temperature. After the start of the reaction, cooling water is passed through the exchanger 3. Within 15 minutes, about 75% of the theoretical quantity≈33 m$^3$ of hydrogen is absorbed. The hydrogenation is completed after about 3 hours. A sample of the batch, analyzed by gas chromatography (GC) showed quantitative hydrogenation. After cooling the batch to room temperature, the catalyst with the separated sodium chloride was filtered off. Thereafter, the ammoniacal methanol-water mixture was removed by distillation under vacuum at ~300 mbar, and the viscous residue was filtered off from the separated sodium chloride. Subsequent distillation over a falling-film evaporator at bp$_{0.5}$ 125°–130° C. resulted in a yield of serinol of 74% with a purity (GC) of 98.7% by weight.

EXAMPLES 2–7

Analogously to Example 1, the experiments set forth in the following Table were conducted in a 50-liter (Examples 2–4) and 1,400-liter (Examples 5–7) loop-type reactor, respectively:

TABLE

| Example No. | Actual Values Temp. °C. | Actual Values H₂ Pressure bar | Starting Materials Aci Salt × 2CH₃OH kg | Starting Materials CH₃OH kg | Starting Materials Catalyst 5% Pd/C kg | NH₄Cl % of Equiv. | Hydrogen Absorption Actual m³ | Hydrogen Absorption Desired m³ | Serinol Content as per GC in % |
|---|---|---|---|---|---|---|---|---|---|
| 2 | 52 | 30 | 7.00 | 29.2 | 0.34 | 100 | 1.85 | 2.02 | 79.8 |
| 3 | 55 | 30 | 7.00 | 29.0 | 0.35 | 100 | 1.85 | 2.02 | 84.0 |
| 4 | 58 | 39.5 | 7.00 | 29.0 | 0.35 | 100 | 1.85 | 2.02 | 85.6 |
| 5 | 56 | 60 | 180 | 705 | 8.3 | 100 | 47.0 | 46.8 | 84.5 |
| 6 | 58 | 60 | 180 | 700 | 8.3 | 100 | 47.0 | 46.8 | 94.5 |
| 7 | 65 | 60 | 180 | 700 | 8.3 | 100 | 48.0 | 46.8 | 74.6 |

EXAMPLE 8

In a 750-liter stainless steel agitator-equipped vessel, a mixture of 50.0 kg (819 moles) of nitromethane, 103.0 kg of methanol, 50.4 kg (1,663 moles) of paraformaldehyde, and 0.3 kg of 33% by weight potassium hydroxide solution is heated for 15 minutes to 65° C. and, thereafter, cooled to 15° C. Within 3 hours, 166.7 kg (925.8 moles) of 30% by weight sodium methylate solution is added in metered quantities at 15°–20° C., the solution becoming turbid due to the separation of sodium salt of 2-nitro-1,3-propanediol.

The resultant suspension with a theoretical content of 161–168 kg of the sodium salt of 2-nitro-1,3-propanediolx2 CH₃OH (aci salt) is filled into a 1,400-liter loop-type reactor. This suspension is combined with 317 kg of methanol, 49.5 kg of ammonium chloride, and 10.0 kg of catalyst, 5% Pd/C (50% water-moist). This mixture is heated while adding hydrogen to 58° C. Within 10 minutes, 70% of the hydrogen is absorbed. Then the hydrogenation is effected according to Example 1 with further addition of hydrogen at 58° C. and 65 bar. After about 4 hours, the hydrogenation is completed. The reaction mixture is worked up in accordance with Example 1, yielding at bp₁ 128°–135° C. a yellowish-colored, viscous liquid which solidifies after a few hours. The serinol yield is 75% of theory, calculated on the basis of nitromethane utilized. Purity (GC) is 98.7%.

EXAMPLE 9

According to Example 8, a suspension of 2-nitro-1,3-propanediol is prepared, combined with 49.5 kg of ammonium chloride, and fed in metered quantities within 3.5 hours under the hydrogenation conditions of Example 8 into the hydrogenation chamber of a 1,400-liter loop-type reactor containing 400 kg of methanol and 10 kg of catalyst, 5% Pd/C (50% water-moist) at 58° C. After hydrogenation was completed, analysis (GC) showed a more than 95% yield. Purity: 98.8%.

What is claimed is:

1. A process for the preparation of 2-aminopropanediol-1,3 which comprises effecting catalytic hydrogenation of an alkali salt of 2-nitro-1,3-propanediol in the presence of inert solvents and a buffered acid at elevated temperatures and under pressures of 1–98 bar hydrogen in a batch reactor and maintaining a narrow range of temperatures extending from 50° to 80° C. during the reaction by controlled cooling of the reactant medium with a cooling device.

2. A process according to claim 1, wherein the temperatures range is preferably from 55° C. to 60° C.

3. A process according to one of claims 1 or 2, wherein the hydrogenation is conducted in a temperature-controllable reactor with a ring conduit extending from the reactor and with an external heat exchanger operating as the cooling device.

4. A process according to claim 3, wherein the hydrogen is fed via a mixing nozzle arranged at the inlet of the ring conduit into the reactor.

5. A process according to claim 1, wherein a suspension or solution of the starting material containing the 2-nitro-1,3-propanediol is fed in metered quantities during the reaction into a hydrogenation chamber of the reactor while maintaining the required temperature and pressure.

6. A process according to claim 1, wherein a batch process, at least 50% of the required hydrogen is introduced within 15 minutes after onset of the reaction.

7. A process according to claim 1, wherein the temperature of the reaction medium is maintained by recycling the reaction products and unreacted reactants as well as inert solvents and buffered acid through a cooling device, said reaction medium being maintained at isothermic conditions in a temperature range of from 55° to 60° C.

* * * * *